United States Patent
Kim et al.

(10) Patent No.: US 12,084,805 B2
(45) Date of Patent: Sep. 10, 2024

(54) DEODORIZATION MODULE AND DRYING APPARATUS INCLUDING A DEODORIZATION MODULE

(71) Applicant: SEOUL VIOSYS CO., LTD., Gyeonggi-do (KR)

(72) Inventors: Ji Won Kim, Gyeonggi-do (KR); Jae Hak Jeong, Gyeonggi-do (KR); Sang Chul Shin, Gyeonggi-do (KR); Woong Ki Jeong, Gyeonggi-do (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 432 days.

(21) Appl. No.: 16/935,462

(22) Filed: Jul. 22, 2020

(65) Prior Publication Data
US 2020/0345887 A1 Nov. 5, 2020

Related U.S. Application Data

(63) Continuation of application No. PCT/KR2019/000779, filed on Jan. 18, 2019.

(30) Foreign Application Priority Data

Jan. 22, 2018 (KR) ........................ 10-2018-0007653

(51) Int. Cl.
*A61L 9/20* (2006.01)
*D06F 58/20* (2006.01)

(52) U.S. Cl.
CPC .............. *D06F 58/20* (2013.01); *A61L 9/205* (2013.01)

(58) Field of Classification Search
CPC ........ D06F 58/20; D06F 58/02; D06F 58/203; D06F 58/34; A61L 9/205; A61L 9/20;
(Continued)

(56) References Cited

U.S. PATENT DOCUMENTS 7,276,100 B2 * 10/2007 Huehn ...................... F24F 8/10
55/471
8,658,101 B1 * 2/2014 Burnett ................ G02B 5/0891
422/24
(Continued)

FOREIGN PATENT DOCUMENTS

CN 104109970 A 10/2014
CN 104674530 A 6/2015
(Continued)

OTHER PUBLICATIONS

English Translation of KR20160054731A, Lee et al. (Year: 2016).*
(Continued)

*Primary Examiner* — Xiuyu Tai
(74) *Attorney, Agent, or Firm* — Perkins Coie LLP

(57) ABSTRACT

A deodorization module includes an upper housing having an open top and an open bottom; a lower housing coupled to the upper housing; a photocatalytic filter located inside a flow channel and accommodated in the upper housing via the open top of the upper housing; a light source unit located outside the flow channel and comprising at least one light source for emitting ultraviolet rays towards the photocatalytic filter, and a substrate on which the at least one light source is mounted; and a transparent member located between the photocatalytic filter and the light source unit and accommodated in the upper housing via the open bottom of the upper housing.

20 Claims, 21 Drawing Sheets

(58) Field of Classification Search
CPC ..... A61L 9/16; A61L 9/18; A61L 9/00; A61L 2/00; A61L 2209/111; B01J 23/70; B01J 37/0215; B01J 23/6527; B01J 23/48; B01J 23/10; B01J 23/40; B01J 35/39; B01J 23/745; B01J 23/14; B01J 23/888; B01J 37/04; B01J 23/30; B01J 21/063; B01J 37/0244; B01J 35/30; B01J 37/347; B01D 2255/802; B01D 2257/90; B01D 53/885

See application file for complete search history.

(56) References Cited

U.S. PATENT DOCUMENTS

| | | | | |
|---|---|---|---|---|
| 9,571,031 | B2* | 2/2017 | Cavieres | F24S 25/632 |
| 2006/0129432 | A1* | 6/2006 | Choi | A61B 5/0002 |
| | | | | 600/300 |
| 2007/0153154 | A1* | 7/2007 | Lee | G02F 1/133608 |
| | | | | 349/58 |
| 2009/0041632 | A1* | 2/2009 | Day | A61L 9/205 |
| | | | | 422/121 |
| 2009/0179547 | A1* | 7/2009 | Auday | A61L 2/10 |
| | | | | 313/485 |
| 2010/0260644 | A1* | 10/2010 | Day | A61L 9/205 |
| | | | | 29/527.4 |
| 2012/0218743 | A1* | 8/2012 | Ioka | F21K 9/23 |
| | | | | 362/157 |
| 2012/0219459 | A1 | 8/2012 | Nakatani | |
| 2012/0285459 | A1* | 11/2012 | Sata | F24F 8/10 |
| | | | | 128/205.27 |
| 2014/0234163 | A1* | 8/2014 | Faurie | A61L 9/205 |
| | | | | 422/4 |
| 2015/0359922 | A1* | 12/2015 | Kim | A61L 9/20 |
| | | | | 422/121 |
| 2016/0129432 | A1* | 5/2016 | Ozaki | B01J 23/72 |
| | | | | 502/309 |
| 2018/0280559 | A1* | 10/2018 | Sambandan | B01J 23/70 |
| 2019/0321502 | A1* | 10/2019 | Kim | A61L 9/205 |

FOREIGN PATENT DOCUMENTS

| | | | |
|---|---|---|---|
| CN | 204785889 U | * | 11/2015 |
| CN | 105530965 A | | 4/2016 |
| CN | 106758062 A | | 5/2017 |
| EP | 2759632 A1 | | 7/2014 |
| JP | 2007-144381 | | 6/2007 |
| JP | 2009295578 A | | 12/2009 |
| JP | 2017148202 A | | 8/2017 |
| KR | 20020080734 A | | 10/2002 |
| KR | 20050098574 A | | 10/2005 |
| KR | 10-2015-0087496 | | 7/2015 |
| KR | 10-1561981 | | 10/2015 |
| KR | 20160054731 A | * | 5/2016 |
| KR | 10-2018-0004979 | | 1/2018 |
| WO | WO-2013079462 A1 | * | 6/2013 ......... A47L 15/4276 |
| WO | 2016147792 | | 9/2016 |
| WO | 2016175274 A1 | | 11/2016 |

OTHER PUBLICATIONS

English Translation of JP2016530908A1, Tail Takashi et al. (Year: 2016).*
English Translation of CN-204785889-U, Kong et al. (Year: 2015).*
English Translation of WO-2013079462-A1, Schaub, H. (Year: 2013).*
English Translation of WO-2017099231-A1, Hiroyuki, W. (Year: 2017).*
English Translation of WO-2015002324-A1, Fukumura, T. (Year: 2015).*
Lee et al. (KR 20160054731 A, machine translation) (Year: 2016).*
Ma et al. (CN 204785889 U, machine translation) (Year: 2015).*
Schaub et al. (WO 2013079462, machine translation) (Year: 2013).*
European Search Report issued in corresponding European Application No. 19741653.0, mailed Sep. 24, 2021, 8 pages.
English translation of Office Action issued on Oct. 8, 2021, in counterpart Chinese Application No. 201980003182.9, 8 pages.
International Search Report for International Application PCT/KR2019/000779, mailed May 22, 2019.
English translation of Korean Office Action from corresponding Korean Patent Application No. 1020180007653 dated Nov. 27, 2022.
English translation of Japanese Office Action from corresponding Japanese Patent Application No. 2020-539268 dated Nov. 30, 2022.

* cited by examiner

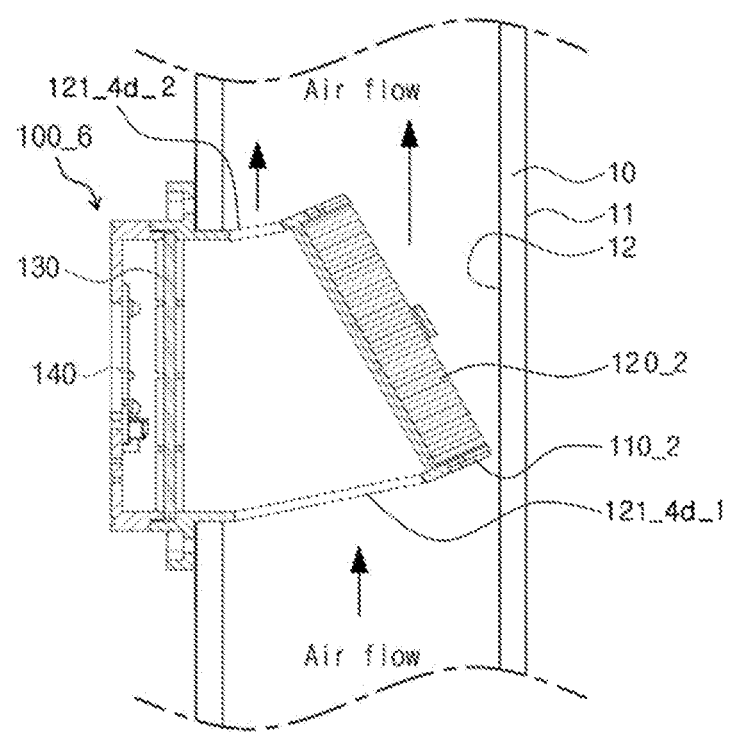

DEODORIZATION MODULE AND DRYING APPARATUS INCLUDING A DEODORIZATION MODULE

CROSS-REFERENCE TO RELATED APPLICATIONS AND PRIORITY

This application is a continuation of PCT/KR2019/000779 filed on Jan. 18, 2019, which claims the benefit of Korean Patent Application No. 10-2018-0007653, filed on Jan. 22, 2018, in the Korean Intellectual Property Office, the disclosures of which are incorporated herein in their entireties by reference.

TECHNICAL FIELD

Embodiments of the present disclosure relate to a deodorization module and, more particularly, to a deodorization module applied to a dryer or a washing machine supporting a drying function to perform a deodorization operation.

BACKGROUND

Recently, a washing machine supporting a drying function is generally used in daily life. The washing machine supporting the drying function removes contaminants from clothes using water and a detergent, and dries wet clothes using hot air, thereby saving a user the hassle of taking wet clothes out of the washing machine and separately drying the clothes on a drying rack.

However, the washing machine supporting the drying function has a drawback of being susceptible to odor. For example, if the drying function of the washing machine may be performed without cleaning for a long period of time and contaminated with contaminants, odor particles activated by hot air are attached to the clothes. In this case, unpleasant odor remains on the washed clothes.

SUMMARY

Embodiments of the present disclosure provide a deodorization module applied to a dryer or a washing machine supporting a drying function to perform a deodorization operation. In accordance with embodiments of the present disclosure, a deodorization module provided to a flow channel includes: an upper housing open at top surface and lower surface thereof; a lower housing coupled to the upper housing;

a photocatalytic filter disposed inside the flow channel to be received in the upper housing through the open top surface of the upper housing; a light source unit disposed outside the flow channel and including at least one light source adapted to emit ultraviolet light towards the photocatalytic filter and a substrate on which the at least one light source is mounted; and a transparent member disposed between the photocatalytic filter and the light source unit and received in the upper housing through the open lower surface of the upper housing.

According to one embodiment, the lower housing may have an open top surface and the light source unit may be received in the lower housing through the open top surface of the lower housing.

According to one embodiment, the upper housing may include: a filter securing portion protruding from an upper portion of the upper housing and securing one surface of the photocatalytic filter; and a filter seating portion protruding along an inner side surface of the upper housing such that the other surface of the photocatalytic filter is seated on the filter seating portion.

According to one embodiment, the upper housing may further include: at least one opening formed at a lower end of the filter seating portion to expose the interior of the upper housing; and at least one rib formed in the at least one opening.

According to one embodiment, the upper housing may further include a spacer protruding from a lower end of the at least one opening and contacting one surface of the transparent member.

According to one embodiment, the lower housing may include a spacer protruding from an upper end of the lower housing and contacting the other surface of the transparent member.

According to one embodiment, the lower housing may include at least one securing protrusion protruding from a lower surface of the lower housing and securing the light source unit.

According to one embodiment, the lower housing may further include: a heat dissipation hole formed on the lower surface of the lower housing and corresponding to a shape of the light source unit; and a withdrawal hole through which an electric wire connected to the light source unit is extracted outside.

According to one embodiment, air inside the flow channel may be brought into contact with the one surface of the photocatalytic filter through the open top surface of the upper housing and with the other surface of the photocatalytic filter through the at least one opening.

According to one embodiment, the deodorization module may further include a heat dissipation member contacting the light source unit and discharging heat from the light source unit.

According to one embodiment, the substrate may be a heat dissipation substrate.

According to one embodiment, the deodorization module may further include a reflective plate disposed inside the flow channel and reflecting light emitted from the light source unit.

According to one embodiment, the reflective plate may be slanted at a predetermined angle with respect to the photocatalytic filter.

According to one embodiment, the deodorization module may further include a flow channel guide disposed inside the flow channel to be slanted at a predetermined angle with respect to the photocatalytic filter and having at least one surface coated with a reflective material.

According to one embodiment, air inside the flow channel may flow in a first direction and the photocatalytic filter may be disposed to extend in a second direction perpendicular to the first direction.

According to one embodiment, the air inside the flow channel may flow in a first direction and the photocatalytic filter may be slanted at a predetermined angle with respect to the first direction.

According to one embodiment, the light source unit may be disposed parallel to the photocatalytic filter slanted at a predetermined angle with respect to the first direction.

In another embodiment, a deodorization module provided to a flow channel, includes an upper housing open at top surface and lower surface thereof; a lower housing coupled to the upper housing; and a photocatalytic filter received in the upper housing through the open top surface of the upper housing. The deodorization module further includes a light source unit comprising at least one light source adapted to emit ultraviolet light towards the photocatalytic filter and a substrate on which the at least one light source is mounted; and a transparent member disposed between the photocatalytic filter and the light source unit and received in the upper housing through the open lower surface of the upper housing. The deodorization module is arranged in and adjacent to the flow channel such that at least a part of the photocatalytic filter is disposed inside the flow channel and the light source unit is disposed outside the flow channel.

In accordance with embodiments of the present disclosure, a drying apparatus may include: a drum into which laundry is input; a drying heater heating air supplied into the drum; a flow channel along which hot air heated by the drying heater is supplied into the drum; a blower fan blowing hot air heated by the drying heater to flow into the drum; and a deodorization module provided to the flow channel and deodorizing the hot air, wherein the deodorization module includes: an upper housing open at top surface and lower surface thereof; a lower housing coupled to the upper housing; a photocatalytic filter disposed inside the flow channel to be received in the upper housing through the open top surface of the upper housing; a light source unit disposed outside the flow channel and including at least one light source adapted to emit ultraviolet light towards the photocatalytic filter and a substrate on which the at least one light source is mounted; and a transparent member disposed between the photocatalytic filter and the light source unit and received in the upper housing through the open lower surface of the upper housing.

According to one embodiment, the drying heater and the deodorization module may be simultaneously operated.

According to one embodiment, a deodorization operation of the deodorization module may be performed after completion of a drying operation of the drying heater.

According to embodiments of the present disclosure, the deodorization module may be applied to a washing machine or a dryer to perform a deodorization operation.

BRIEF DESCRIPTION OF DRAWINGS

FIG. 16A through FIG. 16D are views of deodorization modules according to other embodiments of the present disclosure.

FIG. 16A illustrates a deodorization module having a photocatalytic filter crossing air flow according to other embodiments of the present disclosure.

FIG. 16B illustrates a deodorization module having a photocatalytic filter slanted at a certain angle to an air flow direction according to other embodiments of the present disclosure.

FIG. 16C illustrates a deodorization module having a photocatalytic filter in parallel to a light source unit according to other embodiments of the present disclosure.

FIG. 16D illustrates a deodorization module having a semi-circular photocatalytic filter according to other embodiments of the present disclosure.

DETAILED DESCRIPTION OF EMBODIMENTS

Figure 1:
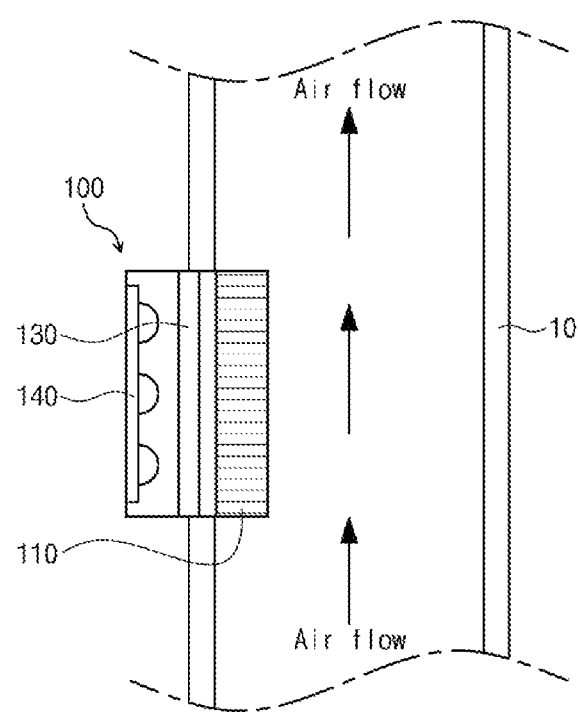
FIG. 1 is a schematic view of a deodorization module provided to a flow channel according to one embodiment of the present disclosure.

The present disclosure may be implemented in various ways and certain embodiments will be described in detail with reference to the accompanying drawings. However, it should be understood that the present disclosure is not limited to the following embodiments and includes all modifications, variations, alterations, and equivalents fallowing within the spirit and scope of the present invention.

Like components are denoted by like reference numerals throughout the specification and accompanying drawings. It should be understood that the drawings are not to precise scale and some of the dimensions, such as width, length, thickness, and the like, are exaggerated for clarity of description. Although terms, such as first, second, etc., may be used herein to describe various elements or components, these elements or components should not be limited by these terms. These terms are used to distinguish one element or component from another element or component. Thus, a first element or component discussed below could be termed a second element or component without departing from the teachings of the present disclosure. As used herein, the singular forms, "a," "an," and "the" are intended to include the plural forms as well, unless the context clearly indicates otherwise.

Moreover, it should be understood that the terms "comprises," "comprising," "includes," and/or "including," as used in this specification, specify the presence of stated features, integers, steps, operations, elements, components, and/or groups thereof, but do not preclude the presence or addition of one or more other features, integers, steps, operations, elements, components, and/or groups.

Next, exemplary embodiments of the present disclosure will be described in detail with reference to the accompanying drawings.

FIG. 1 is a schematic view of a deodorization module 100 according to one embodiment of the present disclosure. As shown in FIG. 1, the deodorization module 100 is provided to a flow channel 10.

In some embodiments, the deodorization module 100 may be provided to the flow channel 10 of a dryer or a washing machine supporting a drying function, and can effectively remove odor particles, which are activated by hot air during a drying operation, through photocatalytic reaction.

Referring to FIG. 1, the deodorization module 100 includes a photocatalytic filter 110 and a light source unit 140.

The photocatalytic filter 110 is disposed inside the flow channel 10 and is coated with or adsorbs a photocatalytic material. The photocatalytic filter 110 may be disposed parallel to a flow direction of air inside the flow channel 10 such that the air inside the flow channel 10 can contact a broad area of the photocatalytic filter 110.

The light source unit 140 is disposed outside the flow channel 10 as shown in FIG. 1 and emits light towards the photocatalytic filter 110. For example, the light source unit 140 may emit light in a UV wavelength band. In this case, a light emitting diode (LED) may be used as a light source for emitting UV light.

In this embodiment, the photocatalytic material coated on the photocatalytic filter 110 performs photocatalytic reaction by UV light emitted from the light source unit 140 and decomposes various contaminants, particularly, odor particles, in air through oxidation and reduction by photocatalytic reaction when the air contacts a photocatalytic material.

More specifically, in drying operation of a typical washing machine or dryer, odor particles are eluted from contaminants in the washing machine or the dryer through activation by hot air and are attached to clothes, thereby causing unpleasant odor of clothes after completion of the drying operation. The deodorization module 100 according to this embodiment removes the odor particles activated by hot air during the drying operation, thereby preventing unpleasant odor from remaining on the washed clothes.

In the deodorization module 100 according to this embodiment, the photocatalytic filter 110 is disposed inside the flow channel 10 and the light source unit 140 is disposed outside the flow channel 10. Accordingly, such arrangement of the light source unit 140 may prevent water molecules in air flowing along the flow channel 10 from entering the light source unit 140 and therefore, damage to the light source unit 140 by hot air may be prevented.

The deodorization module 100 according to this embodiment may further include a transparent member 130. The transparent member 130 is formed of a material allowing light emitted from the light source unit 140 to pass therethrough. The transparent member 130 is placed between the light source unit 140 and the photocatalytic filter 110 to shield the light source unit 140 and the photocatalytic filter 110 from each other. Accordingly, the transparent member 130 can protect the light source unit 140 by preventing a hot air stream and water molecules flowing along the flow channel 10 from entering the light source unit 140 through the photocatalytic filter 110.

Figure 2:
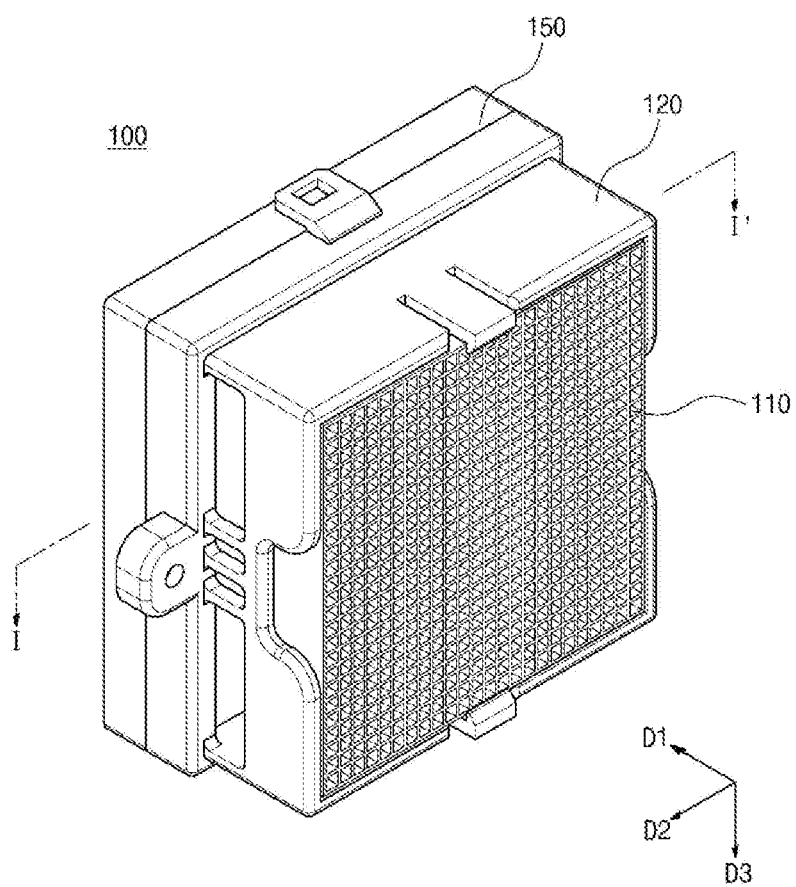
FIG. 2 is a perspective view of a deodorization module 100.
Figure 3:
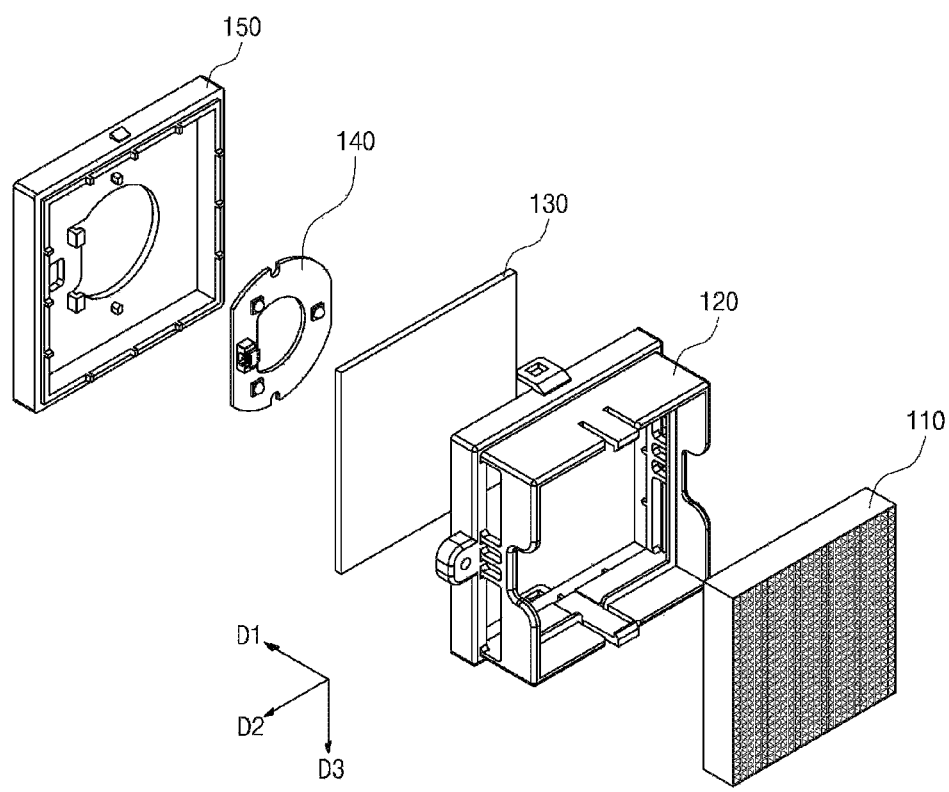
FIG. 3 is an exploded perspective view of the deodorization module 100.
Figure 4:
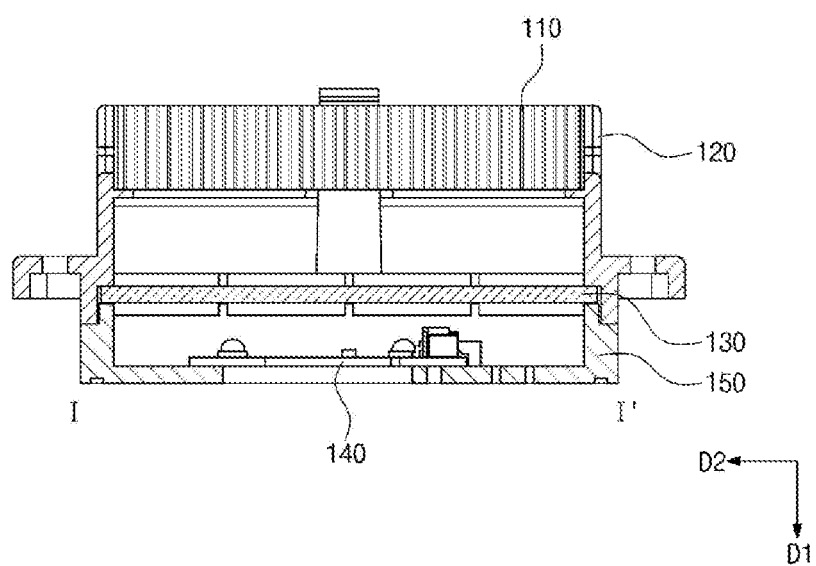
FIG. 4 is a cross-sectional view taken along line I-I of FIG. 2.

FIG. 2 to FIG. 4 are views of the deodorization module 100 shown in FIG. 1. Specifically, FIG. 2 and FIG. 3 are a perspective view and an exploded perspective view of a deodorization module 100, respectively, and FIG. 4 is a cross-sectional view taken along line I-I of FIG. 2.

Referring to FIG. 2 to FIG. 4, the deodorization module 100 includes the photocatalytic filter 110, an upper housing 120, the transparent member 130, the light source unit 140, and a lower housing 150.

The photocatalytic filter 110 may be formed of a material coated with or adsorbing a photocatalytic material. For example, the photocatalytic filter 110 may be formed of a porous ceramic material. In another example, the photocatalytic filter 110 may be formed of a paper material, a fabric material and/or a plastic material. Alternatively, the photocatalytic filter 110 may be formed of a metal foam material containing nickel (Ni), iron (Fe), aluminum (Al), chromium (Cr), stainless steel, and the like.

The surface of the photocatalytic filter 110 may be coated with the photocatalytic material. The photocatalytic material of the photocatalytic filter 110 performs photocatalytic reaction by UV light emitted from the light source unit 140 and decomposes various contaminants, particularly, odor particles, in air through oxidation and reduction by photocatalytic reaction when the air contacts the photocatalytic material.

More specifically, a photocatalyst generates electrons and holes through photocatalytic reaction when exposed to light having energy greater than a band gap or more. As a result, compounds, for example, water or organic materials, in air are decomposed to generate hydroxyl radicals. Hydroxyl radicals have very strong oxidation power and decompose contaminants in air or sterilize bacteria therein. Examples of the photocatalytic material may include titanium oxide ($TiO_2$), zinc oxide (ZnO), tin oxide ($SnO_2$), and the like.

Since electrons and holes generated on the surface of the photocatalyst recombine at a very high recombination rate, there is a limit in use of the electrons and the holes for photochemical reaction. Accordingly, metals, such as Pt, Ni, Mn, Ag, W, Cr, Mo, Zn, and oxides thereof may be added thereto in order to reduce the recombination rate of the holes and the electrons. When the recombination rate of the holes and the electrons is reduced, a contact possibility with a target material to be oxidized and/or decomposed increases, thereby improving reactivity. Further, the band gap of the photocatalytic material may be controlled to improve activity of the photocatalyst. It is possible to achieve sterilization, purification and deodorization of air using such reaction of the photocatalyst.

The upper housing 120 has a structure wherein top surface and lower surface thereof are open and a side surface is partially open when viewed in a first direction D1. The upper housing 120 defines an outer appearance of the deodorization module 100. Further, the upper housing 120 defines a space in which the photocatalytic filter 110 and the transparent member 130 are placed.

The transparent member 130 is received in the upper housing 120 and has a shape corresponding to the upper housing 120. For example, as shown in FIG. 2 to FIG. 4, when the lower surface of the upper housing 120 has a rectangular opening shape, the transparent member 130 may have a rectangular shape corresponding to the shape of the lower surface of the upper housing 120 on which the transparent member 130 is mounted. However, it should be understood that this shape of the transparent member 130 is illustrated by way of example and may be modified in various ways corresponding to the shape of the upper housing 120.

The transparent member 130 is disposed between the photocatalytic filter 110 and the light source unit 140 and shields the photocatalytic filter 110 and the light source unit 140 from each other. For example, as shown in FIG. 1, in a structure wherein the photocatalytic filter 110 is disposed inside the flow channel 10, a hot air stream and/or water molecules may enter the light source unit 140 through the photocatalytic filter 110. In order to prevent the hot air stream and/or the water molecules from entering the light source unit 140 through the photocatalytic filter 110, the transparent member 130 may be disposed between the photocatalytic filter 110 and the light source unit 140, thereby shielding the photocatalytic filter 110 and the light source unit 140 from each other.

Further, referring to FIG. 2 to FIG. 4, the light source unit 140 is disposed inside the lower housing 150 and emits light towards the photocatalytic filter 110. A wavelength band of light emitted from the light source unit 140 may differ depending upon the photocatalytic material coated on the photocatalytic filter 110.

The light source unit 140 may emit light only in some wavelength bands depending upon the photocatalytic material. For example, the light source unit 140 capable of emitting light in the UV wavelength band may emit light in a wavelength band of about 100 nm to about 420 nm. However, it should be understood that this wavelength band is provided by way of example and light emitted from the light source unit 140 is not limited to a particular wavelength band.

For emission of light, the light source unit 140 may include at least one light source that emits light. The light source may be selected from among any light sources emitting light in a wavelength band reacting with the photocatalytic material. For example, for the light source unit 140 emitting light in the UV wavelength band, various light sources that emit UV light may be used. As the light sources emitting UV light, an LED (light emitting diode) may be used. It should be understood that other light sources known in the art may also be used for the light source unit 140 emitting light in other wavelength bands.

The lower housing 150 has a structure wherein the top surface of the lower housing 150 is open and the lower surface thereof is formed with holes, when viewed in the first direction D1. The lower housing 150 defines the outer appearance of the deodorization module 100 together with the upper housing 120. Further, the lower housing 150 defines a space that receives the light source unit 140.

Figure 5:
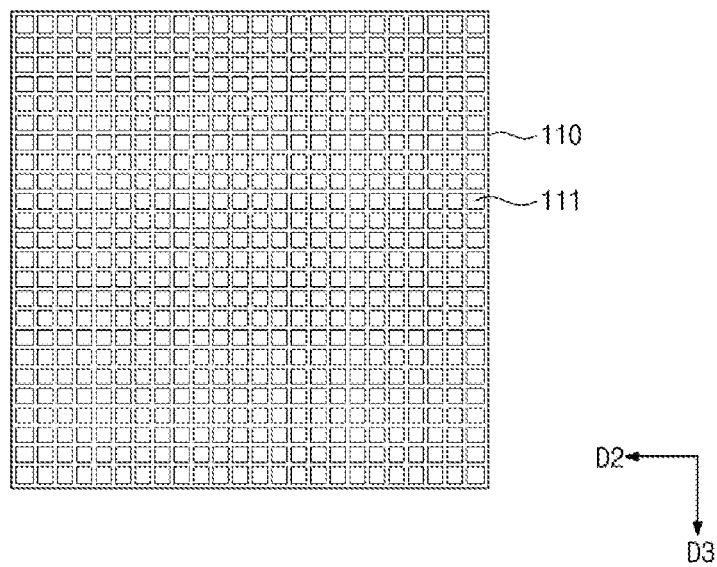
FIG. 5 is a front view of a photocatalytic filter shown in FIG. 3.
Figure 6A:
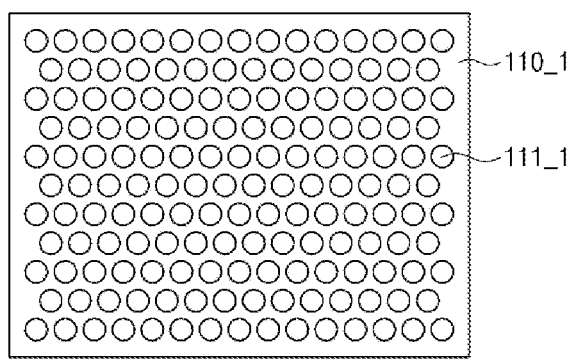
FIG. 6A is a front view of another embodiment of the photocatalytic filter shown in FIG. 3.
Figure 6B:
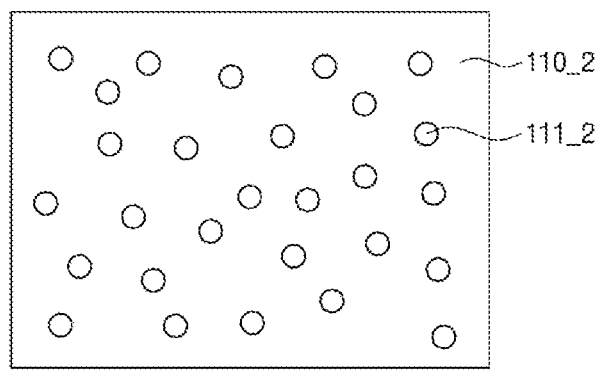
FIG. 6B is a front view of another embodiment of the photocatalytic filter shown in FIG. 3.
Figure 6C:
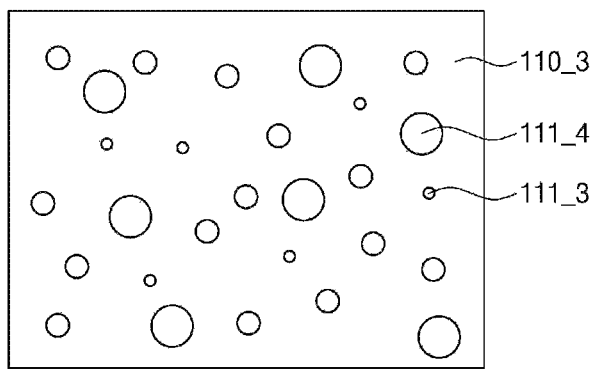
FIG. 6C is a front view of another embodiment of the photocatalytic filter shown in FIG. 3.

FIG. 5 and FIGS. 6A-6C are views of the photocatalytic filter 110 shown in FIG. 3. Specifically, FIG. 5 is a front view of the photocatalytic filter 110 of FIG. 3. FIGS. 6A-6C illustrate a front view of another embodiment of the photocatalytic filter of FIG. 3.

First, referring to FIG. 5, the photocatalytic filter 110 may be formed with a plurality of through-holes 111. Here, each of the plurality of through-holes 111 may be formed in a rectangular opening shape, as shown in FIG. 5. Further, the plurality of through-holes 111 may be regularly arranged in a lattice structure. However, it should be understood that this structure is provided by way of example and the shape, size, structure, and arrangement of the photocatalytic filter 110 may be modified in various ways.

For example, as shown in FIG. 6A, a photocatalytic filter 110_1 may be formed with through-holes 111_1 having a circular shape. In this embodiment, the through-holes 111_1 evenly distribute external pressure along the circular circumference thereof, thereby improving stiffness of the photocatalytic filter 110_1.

In the structure where the through-holes 111_1 are formed in a circular shape, the circular through-holes 111_1 may be arranged in a zigzag arrangement, as shown in FIG. 6A, in order to maximize a contact area of air with the photocatalytic filter 110_1 by forming the through-holes 111_1 as much as possible in the same area. However, it should be understood that this arrangement is provided by way of example and the circular through-holes 111_1 may be regularly arranged in a lattice structure or in a parallel structure.

Alternatively, as shown in FIG. 6B and FIG. 6C, each of photocatalytic filters 110_2, 110_3 may be formed by sintering a plurality of beads. In these embodiments, pores 111_2 to 111_4 may be placed between the sintered beads of each of the photocatalytic filters 110_2, 110_3.

Air can flow from one side of the each of photocatalytic filters 110_2, 110_3 to the other side thereof through the pores 111_2 through 111_4. A contact area between air and the photocatalytic filters 110_2, 110_3 may be adjusted depending upon density of the pores 111_2 to 111_4. To this end, the size of the beads forming the photocatalytic filters 110_2, 110_3 and the sintering conditions of the beads may be adjusted, whereby the pores 111_2 through 111_4 can have various sizes and can be distributed in various ways.

That is, the size and arrangement of the pores 111_2 through 111_4 may be set in various ways in consideration of an air flow rate, reactivity of air with the photocatalyst, and the like. For example, as shown in FIGS. 6B and 6C, in a structure where air flows through the photocatalytic filter 110 in a perpendicular direction with respect to the photocatalytic filter 110, the size and density of the pores 111_2 through 111_4 may be sequentially decreased in order to increase a time for which air resides therein.

In FIGS. 6A-6C, some pores are illustrated for convenience of description and the pores are illustrated as having a spherical shape. However, it should be understood that the pores can be provided in a higher density than that of the pores shown in FIGS. 6A-6C and there can be a difference in size or shape between the pores.

Figure 7:
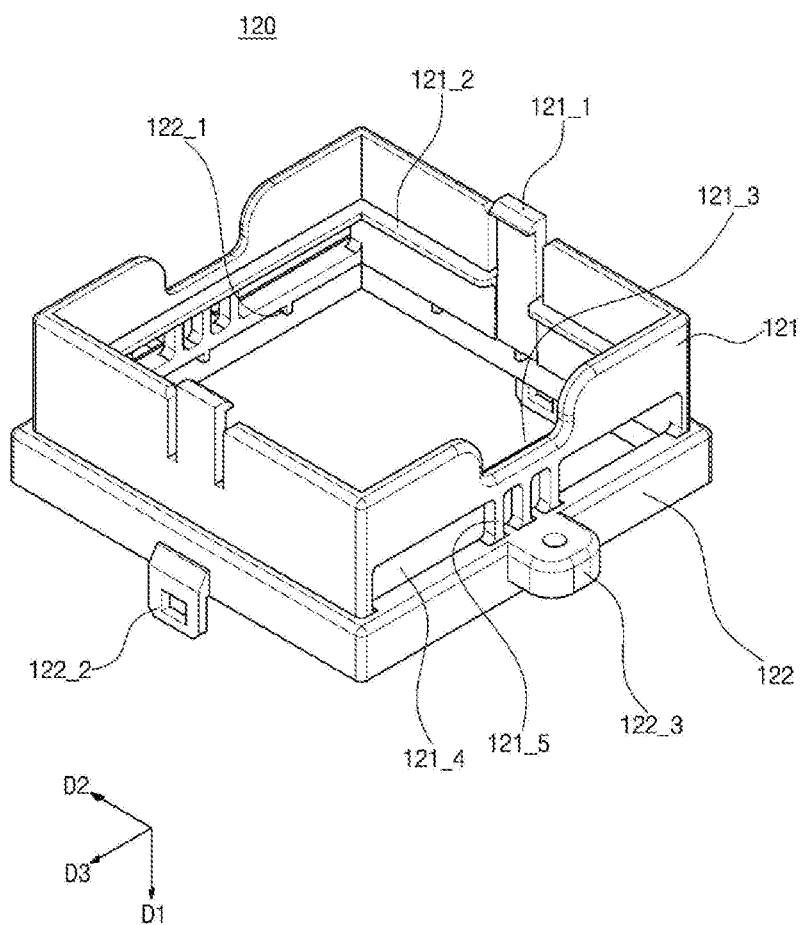
FIG. 7 is a perspective view of an upper housing shown in FIG. 3.

FIG. 7 is a perspective view of the upper housing 120 shown in FIG. 3.

Referring to FIG. 7, the upper housing 120 may be divided into a first body 121 and a second body 122.

The first body 121 has a structure where top surface and lower surface thereof are open, when viewed in the first direction D1. The first body 121 may receive the photocatalytic filter 110 through the open top surface thereof. The first body 121 is formed with filter securing portions 121_1, a filter seating portion 121_2, filter gripping grooves 121_3, openings 121_4, and ribs 121_5.

The filter securing portions 121_1 serve to prevent the photocatalytic filter 110 received in the first body 121 from escaping therefrom. The filter securing portions 121_1 are formed at opposite sides of the first body 121 to face each other and have a hook shape protruding in the first and third directions D1, D3 of the first body 121. However, it should be understood that this structure is provided by way of example and the filter securing portion 121_1 is not particularly limited to a particular shape so long as the filter securing portion 121_1 can stably secure the photocatalytic filter 110.

The filter seating portion 121_2 serves as a support for supporting the photocatalytic filter 110 received in the first body 121. The filter seating portion 121_2 is formed along an inner side surface of the first body 121. However, it should be understood that this structure is provided by way of example and the filter seating portion 121_2 may have any shape so long as the filter seating portion 121_2 can stably support the photocatalytic filter 110.

The filter gripping grooves 121_3 expose a portion of the photocatalytic filter 110 received in the first body 121 so as to allow the photocatalytic filter 110 to be easily gripped upon mounting or replacement of the photocatalytic filter 110. The filter gripping grooves 121_3 may be formed, for example, at opposite sides of the first body 121 to face each other.

The openings 121_4 are formed at a lower end of the first body 121, more specifically at a lower end of the filter seating portion 121_2 to face each other. As shown in FIG. 2, even when the photocatalytic filter 110 is received in the upper housing 120, the openings 121_4 are not blocked by the photocatalytic filter 110 and are formed through the first body 121 in the second direction D2.

The ribs 121_5 are formed in each of the openings 121_4 and serve to support the first body 121. Although three ribs 121_5 are shown in FIG. 7, the number of ribs 121_5 is not particularly limited so long as the ribs can stably support the first body 121.

Referring to FIG. 7, the second body 122 has a structure where top surface and lower surface thereof are open, when viewed in the first direction D1. The second body 122 may receive the transparent member 130 through the open lower surface thereof.

The second body 122 may have a greater length than the first body 121 in each of the second and third directions D2, D3. Accordingly, the transparent member 130 received in the second body 122 may have a greater length than the photocatalytic filter 110 received in the first body 121 in each of the second and third directions D2, D3. Accordingly, the transparent member 130 received in the second body 122 may have a larger size than the photocatalytic filter 110 received in the first body 121, thereby completely blocking water molecules from entering the light source unit 140 through the photocatalytic filter 110.

The second body 122 is formed with spacers 122_1, housing fastening portions 122_2, and flow channel fastening portions 122_3.

Each of the spacers 122_1 protrudes from a step in the first direction D1. The transparent member 130 received through the lower surface of the second body 122 contacts the spacers 122_1 and is separated a predetermined distance from the step by the spacers 122_1.

The housing fastening portions 122_2 extend in the first direction D1 and serve to fasten the upper housing 120 to the lower housing 150. For example, as shown in FIG. 7, the housing fastening portions 122_2 may be formed at opposite sides of the second body 122 to face each other. In addition, each of the housing fastening portions 122_2 may be formed, for example, at a center thereof with a fastening hole.

The flow channel fastening portions 122_3 protrude in the second direction D2. For example, as shown in FIG. 7, the flow channel fastening portions 122_3 may be formed at opposite sides of the second body 122 to face each other.

Figure 8:
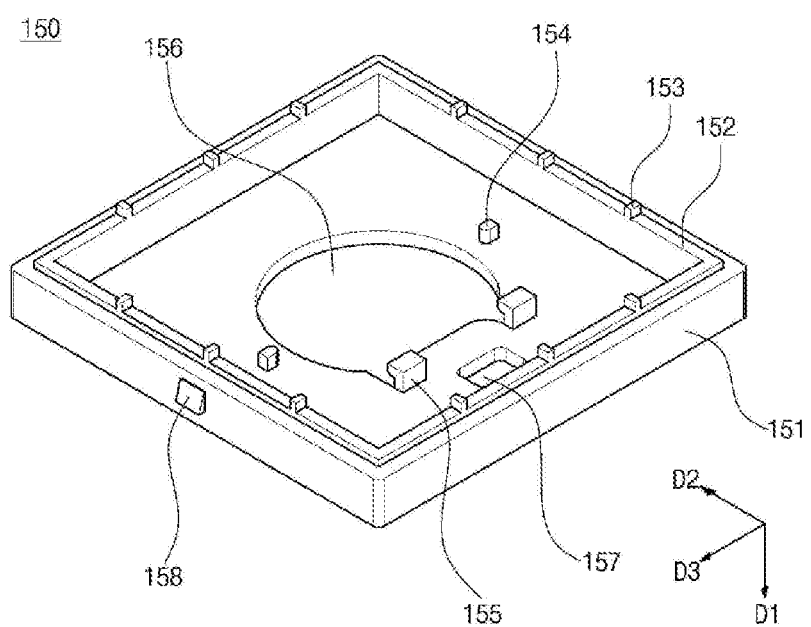
FIG. 8 is a perspective view of a lower housing shown in FIG. 3.

FIG. 8 is a perspective view of the lower housing 150 shown in FIG. 3.

Referring to FIG. 8, the lower housing 150 includes a third body 151, which is open at an upper surface thereof such that the light source unit 140 is received in the third body 151 through the open upper surface thereof. The third body 151 is formed with a step 152, spacers 153, securing protrusions 154, substrate securing portions 155, a heat dissipation hole 156, a withdrawal hole 157, and housing fastening protrusions 158.

The spacers 153 protrude in the first direction D1. The spacers 153 contact the transparent member 130 together with the spacers 122_1 of the upper housing 120. When the lower housing 150 is fastened to the upper housing 120, the spacers 153 of the lower housing 150 and the spacers 122_1 of the upper housing 120 apply pressure towards the transparent member 130 while facing each other, thereby stably securing the transparent member 130.

The securing protrusions 154 protrude in the first direction D1 and are formed in a shape corresponding to securing grooves 144 (see FIG. 9) of the light source unit 140. As the securing protrusions 154 are coupled to the securing grooves 144 of the light source unit 140, the light source unit 140 can be stably secured to the lower housing 150.

On the other hand, two securing protrusions 154 are shown in FIG. 8. However, it should be understood that this structure is provided by way of example and the number of securing protrusions 154 is not particularly limited so long as the securing protrusions 154 can stably secure the light source unit 140.

The substrate securing portions 155 protrude in the first and second directions D1, D2. The substrate securing portions 155 serve to secure a substrate 141 (see FIG. 9) of the light source unit 140. Although two substrate securing portions 155 are shown in FIG. 8, the number of substrate securing portions 155 is not particularly limited so long as the substrate securing portions 155 can stably secure the substrate 141 of the light source unit 140

The heat dissipation hole 156 serves as a path through which heat generated from the light source unit 140 is discharged upon operation of the deodorization module 100. The heat dissipation hole 156 is formed in a shape in which the lower surface of the lower housing 150 is open, when viewed in the first direction. The heat dissipation hole 156 may be formed, for example, at a place corresponding to the substrate 141 of the light source unit 140. However, it should be understood that this structure of the heat dissipation hole 156 is provided by way of example and the shape and location of the heat dissipation hole 156 are not particularly limited so long as the heat dissipation hole 156 can dissipate heat generated from the light source unit 140.

The withdrawal hole 157 serves as a path through which an electric wire connected to a connector 143 of the light source unit 140 is withdrawn outside. The withdrawal hole 157 is formed, for example, in a shape in which the lower surface of the lower housing 150 is open, when viewed in the first direction, without being limited thereto.

The housing fastening protrusions 158 protrude in the third direction D3. The housing fastening protrusions 158 are coupled to the housing fastening portions 122_2 of the upper housing 120 to couple the lower housing 150 to the upper housing 120 as illustrated in FIGS. 2-4, 7, and 11.

Figure 9:
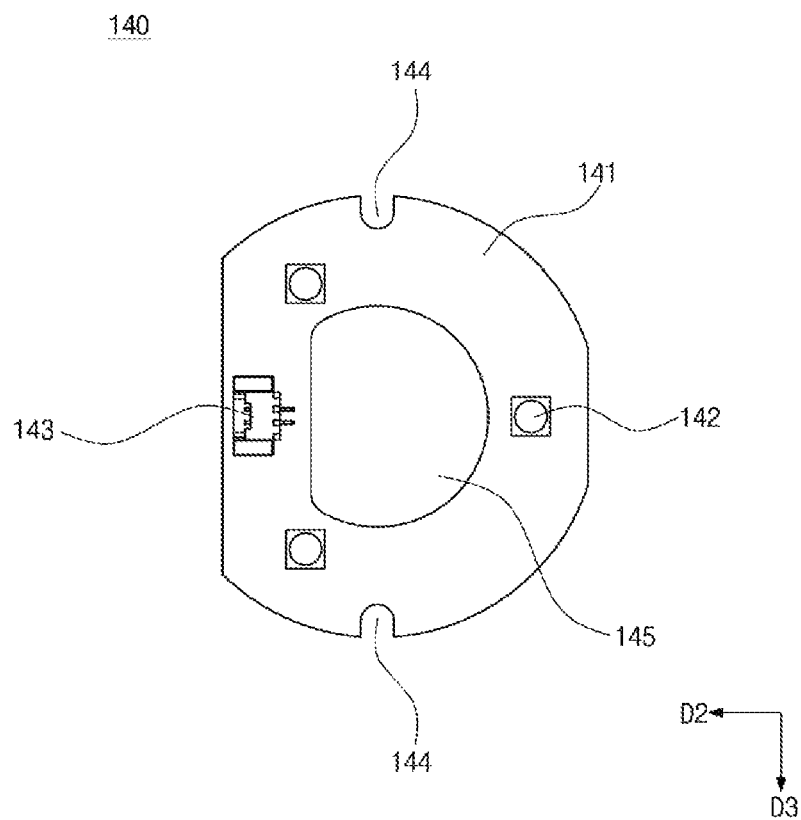
FIG. 9 illustrates a light source mounted on a substrate.
Figure 10A:
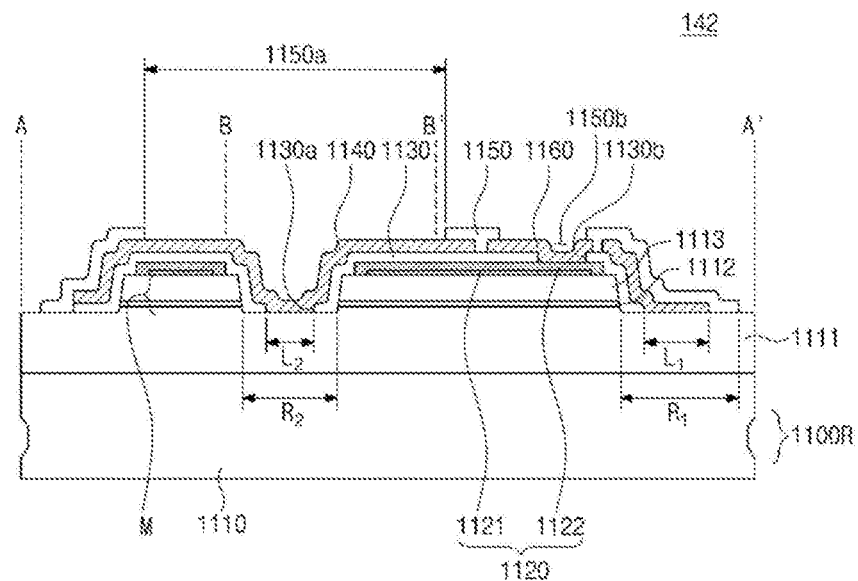
FIG. 10A is a cross-sectional view of the light source.
Figure 10B:
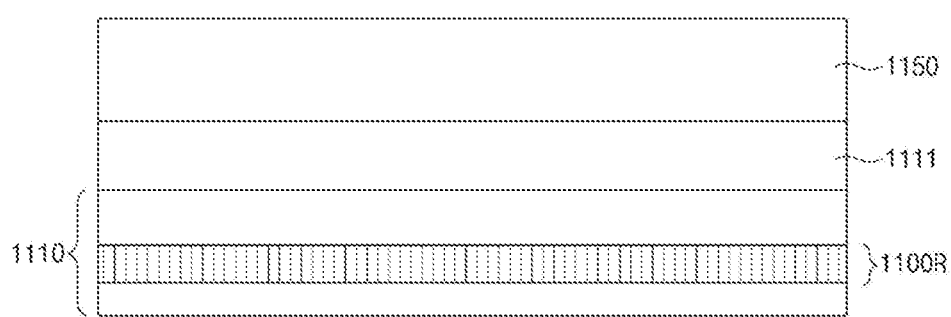
FIG. 10B is a cross-sectional view of the light source taken along line A-B-B'-A' of FIG. 10A.

FIG. 9 to FIGS. 10A and 10B are views of the light source unit 140. Specifically, FIG. 9 is a view of a light source 142 mounted on a substrate 141, and FIG. 10A and FIG. 10B are cross-sectional views of the light source 142.

First, referring to FIG. 9, the light source unit 140 includes a substrate 141, light sources 142, a connector 143, securing grooves 144, and a heat dissipation hole 145.

The light sources 142 are mounted on an upper surface of the substrate 141. The substrate 141 is formed at one side thereof with the connector 143 that supplies electric power to the light sources 142. The substrate 141 is formed at opposite sides thereof with the securing grooves 144 through which the securing protrusions 154 (see FIG. 8) pass when the substrate 141 is secured to the lower housing 150.

The substrate 141 is formed at the center thereof with the heat dissipation hole 145 through which heat is discharged. The substrate 141 may be, for example, a heat dissipation substrate, without being limited thereto. Alternatively, the substrate 141 may be a printed circuit board.

The light sources 142 are mounted on the upper surface of the substrate 141 and emit light towards the photocatalytic filter 110 as illustrated in FIGS. 1-5, 11-13A, 14, and 15. Although three light sources are mounted on the upper surface of the substrate 141 in FIG. 9, it should be understood that the number of light sources 142 is not limited thereto. For example, one light source may be mounted on the upper surface of the substrate 141.

For the light source unit 140 including a plurality of light sources 142, the light sources may emit light in the same wavelength band or in different wavelength bands. For example, each of the light sources may emit light in the UV wavelength band. Alternatively, some light sources may emit light in some bands of the UV wavelength band and the other light sources may emit light in the other bands of the UV wavelength band.

The light sources emitting light in different wavelength bands may be arranged in various sequences. For example, assuming that light sources adapted to emit light in a first wavelength band are referred to as first light sources and light sources adapted to emit light in a second wavelength band are referred to as second light sources, the first light sources and the second light sources may be alternately arranged.

In FIG. 9, each of the light sources 142 includes a lens for protecting a chip therein. However, it should be understood that this structure is provided by way of example and the present disclosure is not limited thereto. For example, the light source 142 may not include the lens. Alternatively, among the plurality of light sources mounted on the substrate 141, some light sources include lenses and the other light sources do not include the lenses.

FIG. 10A is a cross-sectional view of a chip used in the light source 142 according to one embodiment of the present disclosure and FIG. 10B is a cross-sectional view taken along line A-B-B'-A' of FIG. 10A. Referring to FIG. 10A and FIG. 10B, the light source 142 according to the embodiment of the present disclosure includes a first conductivity type semiconductor layer 1111, a mesa M including an active layer 1112 and a second conductivity type semiconductor layer 1113, a first insulation layer 1130, a first electrode 1140, and a second insulation layer 1150, and may further include a growth substrate 1110 and a second electrode 1120.

The growth substrate 1110 may be selected from any substrates that allow the first conductivity type semiconductor layer 1111, the active layer 1112 and the second conductivity type semiconductor layer 1113 to be grown thereon, and may include, for example, a sapphire substrate, a silicon carbide substrate, a gallium nitride substrate, an aluminum nitride substrate, a silicon substrate, and the like. A side surface of the growth substrate 1110 may include an inclined surface to improve extraction of light generated from the active layer 1112.

The second conductivity type semiconductor layer 1113 may be disposed on the first conductivity type semiconductor layer 1111 and the active layer 1112 may be disposed between the first conductivity type semiconductor layer 1111 and the second conductivity type semiconductor layer 1113. The first conductivity type semiconductor layer 1111, the active layer 1112 and the second conductivity type semiconductor layer 1113 may include III-V based compound semiconductors, for example, nitride semiconductors, such as (Al, Ga, In)N. The first conductivity type semiconductor layer 1111 may include n-type dopants (for example, Si) and the second conductivity type semiconductor layer 1113 may include p-type dopants (for example, Mg), or vice versa. The active layer 1112 may include a multi-quantum well (MQM) structure. When forward bias is applied to the light source 142, electrons and holes are recombined in the active layer 1112 to emit light. The first conductivity type semiconductor layer 1111, the active layer 1112 and the second conductivity type semiconductor layer 1113 may be grown on the growth substrate 1110 by metal organic chemical vapor deposition (MOCVD) or molecular beam epitaxy (MBE).

The light source 142 may include at least one mesa M, which includes the active layer 1112 and the second conductivity type semiconductor layer 1113. The mesa M may include a plurality of protrusions separated from each other. Alternatively, the light source 142 (FIG. 9) may include a plurality of mesas M separated from each other. A side surface of the mesa M may be inclined by photoresist reflow and the like to improve luminous efficacy of light generated from the active layer 1112.

The first conductivity type semiconductor layer 1111 may include a first contact region R1 and a second contact region R2, which are exposed through the mesa M. Since the mesa M is formed by removing the active layer 1112 and the second conductivity type semiconductor layer 1113 on the first conductivity type semiconductor layer 1111, portions excluding the mesa M become contact regions on an exposed upper surface of the first conductivity type semiconductor layer 1111. The first electrode 1140 adjoins the first contact region R1 and the second contact region R2 to be electrically connected to the first conductivity type semiconductor layer 1111.

The first contact region R1 may be disposed around the mesa M along an outer periphery of the first conductivity type semiconductor layer 1111, specifically along an outer periphery of the upper surface of the first conductivity type semiconductor layer 1111 between the mesa M and the side surface of the light source 142. The second contact region R2 may be at least partially surrounded by the mesa M.

A major length of the second contact region R2 may be 0.5 times a length of one side of the light source 142 or longer. In this structure, since an adjoining region between the first electrode 1140 and the first conductivity type semiconductor layer 1111 can be increased, electric current flowing from the first electrode 1140 to the first conductivity type semiconductor layer 1111 can be more effectively distributed, thereby further decreasing a forward voltage.

The second electrode 1120 may be disposed on the second conductivity type semiconductor layer 1113 to be electrically connected to the second conductivity type semiconductor layer 1113. The second electrode 1120 may be formed on the mesa M and may have the same shape as the shape of the mesa M. The second electrode 1120 may include a reflective metal layer 1121 and a barrier metal layer 1122, which may cover upper and side surfaces of the reflective metal layer 1121. For example, a pattern of the reflective metal layer 1121 is formed, followed by forming the barrier metal layer 1122 on a pattern of the reflective metal layer 1121 so as to cover the upper and side surfaces of the reflective metal layer 1121. For example, the reflective metal layer 1121 may be formed by depositing an Ag, Ag alloy, Ni/Ag, NiZn/Ag, or TiO/Ag layer, followed by patterning.

On the other hand, the barrier metal layer 1122 may be formed of Ni, Cr, Ti, Pt, Au or a combination thereof. Specifically, the barrier metal layer 1122 may be a combination layer of Ni/Ag/[Ni/Ti]2/Au/Ti sequentially formed on the second conductivity type semiconductor layer 1113. More specifically, at least part of an upper surface of the second electrode 1120 may include a Ti layer having a thickness of 300 Å. When a region of the upper surface of the second electrode 1120 adjoining the first insulation layer is composed of the Ti layer, bonding strength between the first insulation layer 1130 and the second electrode 1120 is increased, thereby improving reliability of the light source 142.

An electrode protective layer 1160 may be disposed on the second electrode 1120. The electrode protective layer 1160 may be formed of the same material as the first electrode 1140, without being limited thereto.

The first insulation layer 1130 may be disposed between the first electrode 1140 and the mesa M. The first insulation layer 1130 may insulate the first electrode 1140 from the mesa M and may insulate the first electrode 1140 from the second electrode 1120. The first insulation layer 1130 may partially expose the first contact region R1 and the second contact region R2. Specifically, the first insulation layer 1130 may partially expose the second contact region R2 through an opening 1130a and may cover only some region of the first contact region R1 between the outer periphery of the first conductivity type semiconductor layer 1111 and the mesa M to expose at least a portion of the first contact region R1.

The first insulation layer 1130 may be disposed along the outer periphery of the second contact region R2 on the second contact region R2. At the same time, the first insulation layer 1130 may be restrictively disposed to be closer to the mesa M than an adjoining region between the first contact region R1 and the first electrode 1140.

The first insulation layer 1130 may have an opening 1130b that exposes the second electrode 1120. The second electrode 1120 may be electrically connected to a pad or bump through the opening 1130b.

The adjoining region between the first contact region R1 and the first electrode 1140 is disposed along the entire outer periphery of the upper surface of the first conductivity type semiconductor layer. Specifically, the adjoining region between the first contact region R1 and the first electrode 1140 may be disposed to be adjacent to all of four sides of the first conductivity type semiconductor layer 1111 and may surround the entirety of the mesa M. In this structure, since the adjoining region between the first electrode 1140 and the first conductivity type semiconductor layer 1111 can be increased, electric current flowing from the first electrode 1140 to the first conductivity type semiconductor layer 1111 can be more effectively distributed, thereby further decreasing forward voltage.

In one embodiment of the present disclosure, the first electrode 1140 and the second electrode 1120 of the light source 142 may be directly mounted on the substrate 141 or may be mounted thereon through pads.

For example, for the first and second electrodes mounted on the substrate 141 through the pads, two pads may be disposed between the light source 142 and the substrate 141 to adjoin the first electrode 1140 and the second electrode 1120, respectively. For example, the pads may be solders or a eutectic metal, without being limited thereto. For example, AuSn may be used as the eutectic metal.

Alternatively, for the light source 142 directly mounted on the substrate 141, the first electrode 1140 and the second electrode 1120 of the light source 142 may be directly bonded to wires on the substrate 141. In this case, a bonding material may include a bonding material having conductivity. For example, the bonding material may include at least one conductive material selected from among silver (Ag), tin (Sn), and copper (Cu). However, it should be understood that these materials are provided by way of example and the bonding material may include various materials having conductivity.

As described with reference to FIG. 1 to FIG. 10, the deodorization module 100 according to this embodiment may be provided to the flow channel 10 of a washing machine, a drum type washing machine or a dryer, and may perform an effective deodorization operation through photocatalytic reaction.

On the other hand, it should be understood that the structure of the deodorization module 100 shown in FIG. 1 to FIG. 10 is provided by way of example and the technical idea of the present disclosure is not limited thereto. For example, the deodorization module 100 according to the present disclosure may be modified and applied in various ways to be provided to the flow channel 10. Next, application and modification of deodorization modules according to various embodiments of the present disclosure will be described.

Figure 11:
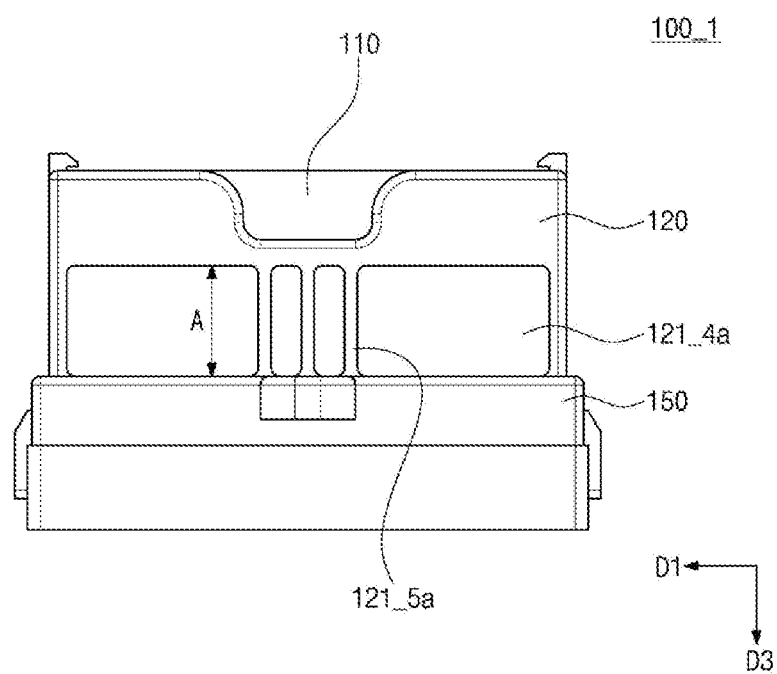
FIG. 11 is a side view of a deodorization module according to another embodiment of the present disclosure.
Figure 12:
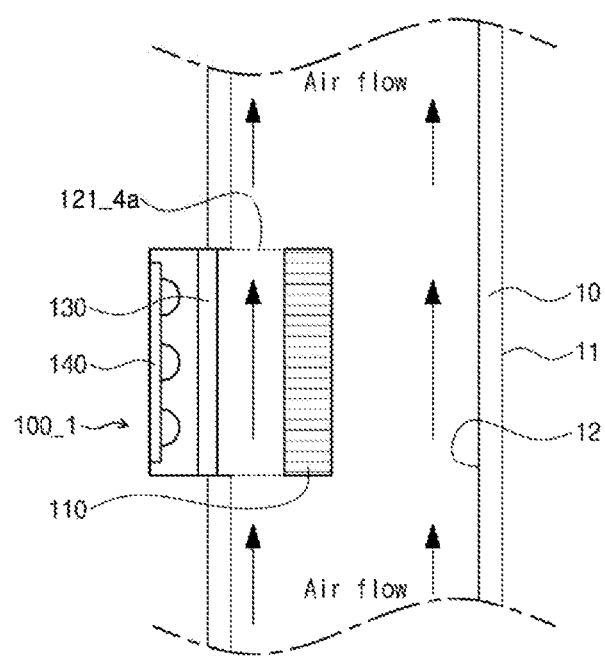
FIG. 12 is a cross-sectional view of the deodorization module provided to a flow channel as shown in FIG. 11.

FIG. 11 is a side view of a deodorization module 100_1 according to another embodiment of the present disclosure and FIG. 12 is a cross-sectional view of the deodorization module of FIG. 11 provided to a flow channel 10.

The deodorization module 100_1 shown in FIG. 11 and FIG. 12 is similar to the deodorization module 100 shown in FIG. 1 to FIG. 10. Thus, the same or similar components are denoted by the same or similar reference numerals and repeated description will be omitted for convenience.

Referring to FIG. 11, the deodorization module 100_1 has slightly larger openings 121_4a than the deodorization module 100 shown in FIG. 1 to FIG. 10. In addition, ribs 121_5a of the deodorization module 100_1 shown in FIG. 11 may have a greater length A than the ribs 121_5 of the deodorization module 100 shown in FIGS. 1 to 10. For example, the length of the ribs 121_5a may be in the range of ¼ to ¾ of a diameter of an inner side surface 12 of the flow channel 10.

In this structure, as shown in FIG. 12, the photocatalytic filter 110 of the deodorization module 100_1 may be placed at the center of the flow channel 10. That is, the photocatalytic filter 110 of the deodorization module 100 shown in FIG. 1 is placed near the inner side surface 12 of the flow channel 10, whereas the photocatalytic filter 110 of the deodorization module 100_1 shown in FIG. 12 is spaced apart by a predetermined distance from the inner side surface 12 of the flow channel 10.

Here, since the openings 121_4a of the deodorization module 100_1 define an air flow passage, air inside the flow channel 10 may flow while contacting the opposite sides of the photocatalytic filter 110. As a result, a contact area between air inside the flow channel 10 and the photocatalytic filter 110 increases, thereby improving deodorization efficiency.

Figure 13A:
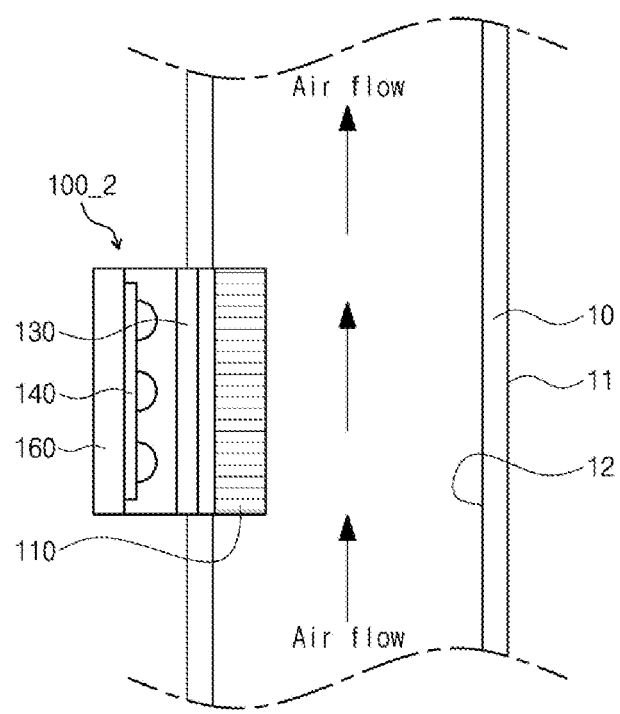
FIG. 13A illustrates one example of a deodorization module including a heat dissipation member.
Figure 13B:
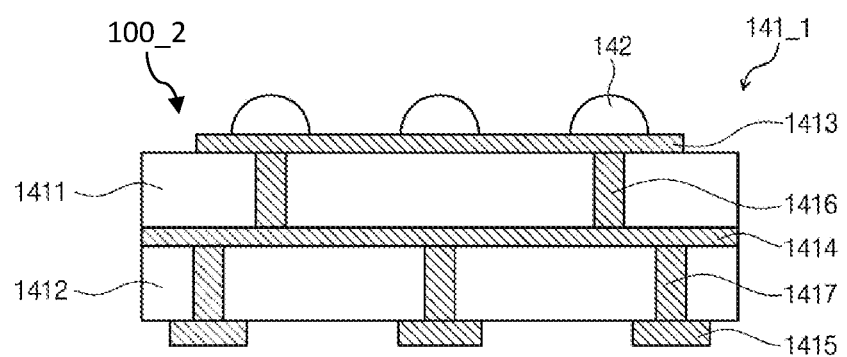
FIG. 13B illustrates one example of a deodorization module including a heat dissipation substrate.

FIGS. 13A and 13B illustrate a deodorization module 100_2 according to a further embodiment of the present disclosure. Specifically, FIG. 13A is a view of one example of the deodorization module 100_2 including a heat dissipation member 160 and FIG. 13B is a view of one example of the deodorization module 100_2 including a heat dissipation substrate 141_1.

The deodorization module 100_2 shown in FIGS. 13A and 13B is similar to the deodorization module 100 shown in FIG. 1 to FIG. 10. Thus, the same or similar components are denoted by the same or similar reference numerals and repeated description will be omitted for convenience.

The deodorization module 100_2 shown in FIG. 13B further includes a heat dissipation structure for dissipation of heat generated from the light source unit 140 unlike the deodorization module 100 shown in FIG. 1 to FIG. 10.

For example, as shown in FIG. 13A, the deodorization module 100_2 may further include a heat dissipation member 160 which discharges heat from the light source unit 140. The heat dissipation member 160 may be, for example, a conductive sheet formed of a conductive material and may serve to discharge heat from the light source unit 140 after distribution of the heat.

Alternatively, as shown in FIG. 13B, the light source unit 140 of the deodorization module 100_2 may include a heat dissipation substrate 141_1. That is, light sources 142 of the deodorization module 100_2 may be mounted on the heat dissipation substrate 141_1.

As shown in FIG. 13B, the heat dissipation substrate 141_1 may include, for example, an upper insulation substrate 1411 and a lower insulation substrate 1412, which are formed of a ceramic material. The upper insulation substrate 1411 and the lower insulation substrate 1412 may be stacked up and down and a bonding material may be used for stacking the insulation substrates. The upper insulation substrate 1411 may have an upper conductive pattern 1413 formed on an upper surface thereof and the lower insulation substrate 1412 may have a lower conductive pattern 1415 formed on a lower surface thereof. Further, an intermediate conductive pattern 14 may be formed between the upper insulation substrate 1411 and the lower insulation substrate 1412. The upper conductive pattern 1413, the intermediate conductive pattern 1414 and the lower conductive pattern 1415 may be formed of a metal, such as Au, Ag, and the like.

As shown in FIG. 13A and FIG. 13B, the deodorization module 100_2 further includes a heat dissipation structure to protect the light source unit 140 (or 142 as illustrated in FIG. 13B) from increase in temperature due to operation of the light source unit 140 (or 142 as illustrated in FIG. 13B) or from increase in temperature due to hot air inside the flow channel 10.

Figure 14:
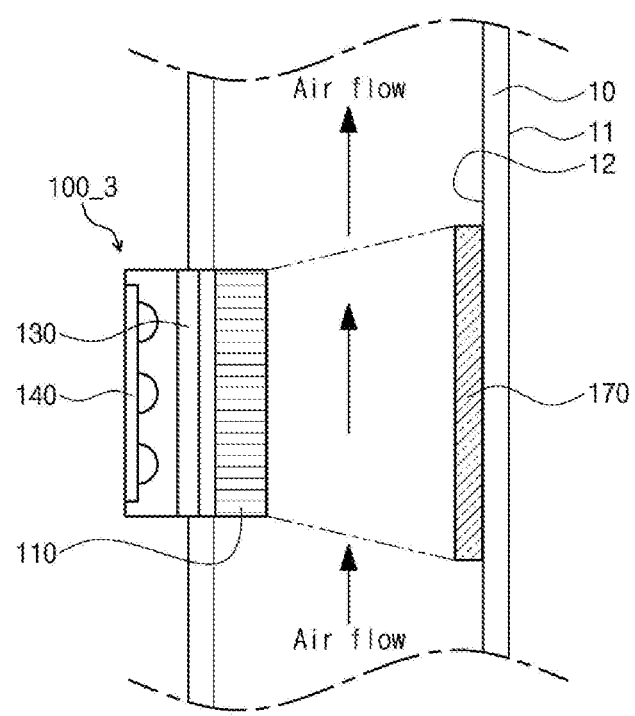
FIG. 14 illustrates a deodorization module according to further another embodiment of the present disclosure.
Figure 15:
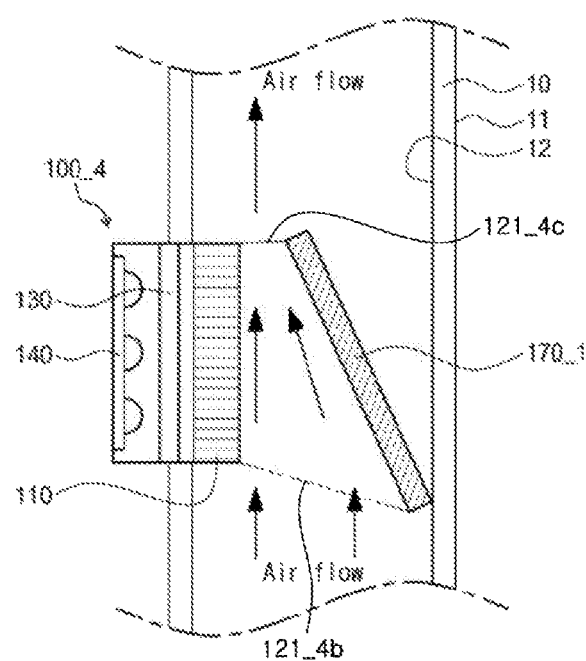
FIG. 15 illustrates a deodorization module according to further another embodiment of the present disclosure.

FIG. 14 and FIG. 15 are views of deodorization modules 100_3, 100_4 according to other embodiments of the present disclosure. Specifically, FIG. 14 is a view of one embodiment of a deodorization module 100_3 including a reflective plate 170 and FIG. 15 is a view of one embodiment of a deodorization module 100_4 including a flow channel guide 170_1 coated with a reflective material.

The deodorization modules 100_3, 100_4 shown in FIG. 14 and FIG. 15 are similar to the deodorization module 100 shown in FIG. 1 to FIG. 10. Thus, the same or similar components are denoted by the same or similar reference numerals and repeated description will be omitted for convenience.

First, referring to FIG. 14, the deodorization module 100_3 further includes the reflective plate 170, which reflects UV light emitted from the light source unit 140. The reflective plate 170 may be formed of, for example, a material having high reflectivity (for example, stainless steel, aluminum, magnesium oxide, Teflon, and the like). Alternatively, the reflective plate 170 may be formed by coating the inner side surface 12 of the flow channel 10 with the material having high reflectivity.

The reflective plate 170 reflects UV light emitted from the light source unit 140 towards the photocatalytic filter 110. Accordingly, the deodorization module 100_3 can prevent loss of UV light due to collision with the inner side surface of the flow channel 10, thereby improving deodorization efficiency of the deodorization module 100_3.

Referring to FIG. 15, the deodorization module 100_4 may include the flow channel guide 170_1, which guides air inside the flow channel 10 to flow towards the photocatalytic filter 110, and one surface of the flow channel guide 170_1 may be coated with a reflective material. That is, as shown in FIG. 15, the flow channel guide 170_1 is slanted at a predetermined angle towards the photocatalytic filter 110 to guide air inside the flow channel 10 to flow towards the photocatalytic filter 110 and one surface of the flow channel guide 170_1 facing the photocatalytic filter 110 may be coated with the reflective material. In this structure, the flow channel guide 170_1 reflects UV light emitted from the light source unit 140 while guiding the air inside the flow channel 10 towards the photocatalytic filter 110. With this structure, the deodorization module 100_4 allows a large amount of air to contact the photocatalytic filter 110, thereby improving deodorization efficiency of the deodorization module 100_4.

Furthermore, in the structure where the flow channel guide 170_1 is slanted at a predetermined angle towards the photocatalytic filter 110, as shown in FIG. 15, an opening 121_4b through which air flows into the flow channel 10 has a larger area than the area of an opening 121_4c through which air is discharged from the flow channel 10, thereby increasing a period of time for which air guided into the photocatalytic filter 110 resides therein. As a result, a time for reaction between air and the photocatalytic filter 110 increases, thereby further improving deodorization efficiency of the deodorization module 100_4.

On the other hand, in FIG. 15, the deodorization module 100_4 includes the flow channel guide 170_1 coated with the reflective material. However, it should be understood that this structure is provided by way of example and the present disclosure is not limited thereto. For example, the deodorization module 100_4 may include a reflective plate, instead of the flow channel guide 170_1 coated with the reflective material. In this structure, the reflective plate may act as the flow channel guide.

FIG. 16A through FIG. 16D are views of deodorization modules 100_5 to 100_8 according to other embodiments of the present disclosure. The deodorization modules 100_5 to 100_8 shown in FIG. 16A through FIG. 16D are similar to the deodorization module 100 shown in FIG. 1 to FIG. 10. Thus, the same or similar components are denoted by the same or similar reference numerals and repeated description will be omitted for convenience.

Figure 16A:
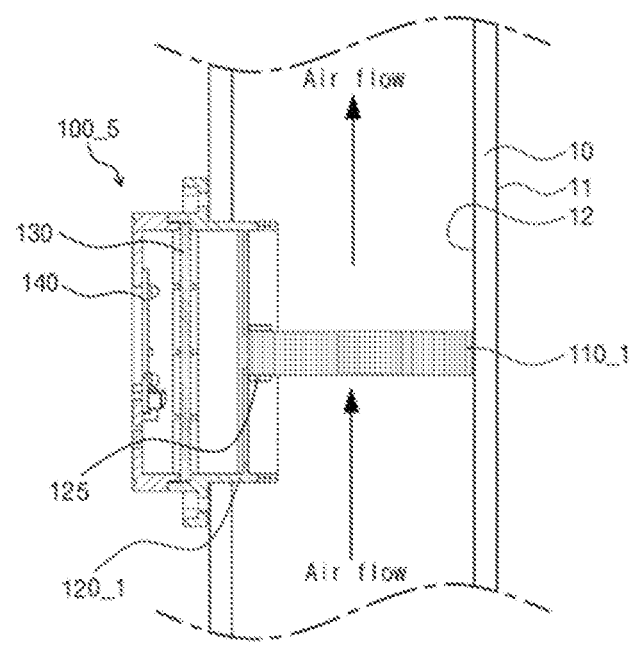

First, referring to FIG. 16A, in the deodorization module 100_5, a photocatalytic filter 110_1 is disposed perpendicular to an air flow direction.

The photocatalytic filter 110_1 is mounted in a slot 125 formed inside an upper housing 120_1 through the open top surface of the upper housing 120_1. For example, the slot 125 may be formed to extend from one inner side surface to the other inner side surface of the upper housing 120_1. As one side surface of the photocatalytic filter 110_1 is coupled to the slot 125, the photocatalytic filter 110_1 can be secured to the upper housing 120_1. In the FIG. 16A, a portion of the upper housing 120_1 located inside the flow channel 10 can be omitted.

In this structure, all air inside the flow channel 10 flows through through-holes formed in the photocatalytic filter 110_1, thereby increasing the amount of air contacting the photocatalytic filter 110_1.

Referring to FIG. 16B, in the deodorization module 100_6, a photocatalytic filter 110_2 is slanted at a predetermined angle with respect to the air flow direction. The openings 121_4d of the deodorization module 100_1 define an air flow passage. For example, an inclination of the photocatalytic filter 110_2 may be set in consideration of a beam angle of light emitted from the light source unit 140. In this structure, all air inside the flow channel 10 passes through the photocatalytic filter 110_2 and a sufficient amount of light is emitted to the photocatalytic filter 110_2, thereby improving deodorization efficiency of the deodorization module 100_6.

Referring to FIG. 16B, a side surfaces of an upper housing 120_2 is bent. For example, the upper housing 120_2 may have a structure in which the side surface and ribs are bendable. Alternatively, the upper housing 120_2 have a structure in which the side surface located on the upper portion and lower portion of the ribs is bent.

Therefore, an open top surface and a photocatalytic filter 110_2 are slanted at a predetermined angle with respect to the air flow direction.

In addition, the rib located one side of the upper housing 120_2 may have a longer length than the rib located the other side of the upper housing 120_2. Therefore, an opening 121_4d_1 through which air is introduced may have a larger area than an opening 121_4d_2 through which air is discharged.

Figure 16C:
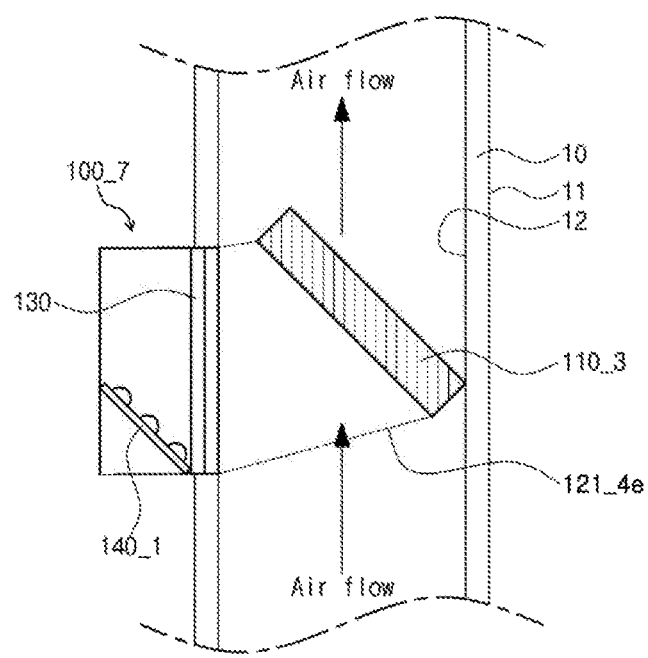

The deodorizing module 100_7 of FIG. 16C is similar to the deodorizing module 100_6 of FIG. 16B except for the position of the light source unit. Hereinafter, the position of a light source unit 140_1 in the deodorization module 100_7 of FIG. 16C will be described below, and descriptions of other elements can be referred to FIG. 16B and the embodiments described above.

Referring to FIG. 16C, in the deodorization module 100_7, a photocatalytic filter 110_3 is slanted at a predetermined angle with respect to the air flow direction and the light source unit 140_1 is disposed parallel to the photocatalytic filter 110_3. The openings 121_4e of the deodorization module 100_1 define an air flow passage. In this structure, a greater amount of light is emitted to the photocatalytic filter 110_3, thereby improving deodorization efficiency of the deodorization module 100_7.

Figure 16D:
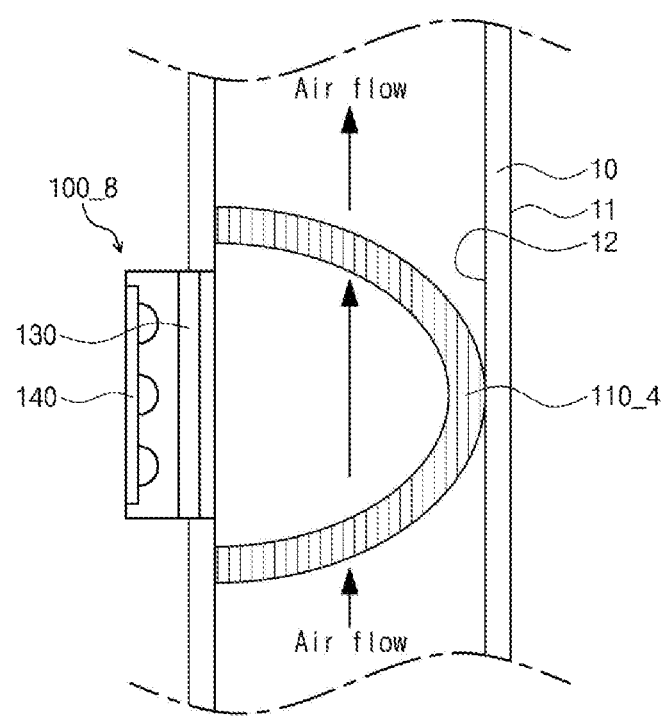

Referring to FIG. 16D, in the deodorization module 100_8 includes a photocatalytic filter 110_4, which has a semi-circular cross-section. For example, the photocatalytic filter 110_4 may be formed of paper, fabrics or metal foam so as to have a semi-circular cross-section. With this structure, the deodorization module 100_8 can increase a contact area between air and the photocatalytic filter 110_1, thereby improving deodorization efficiency of the deodorization module 100_8.

Figure 17:
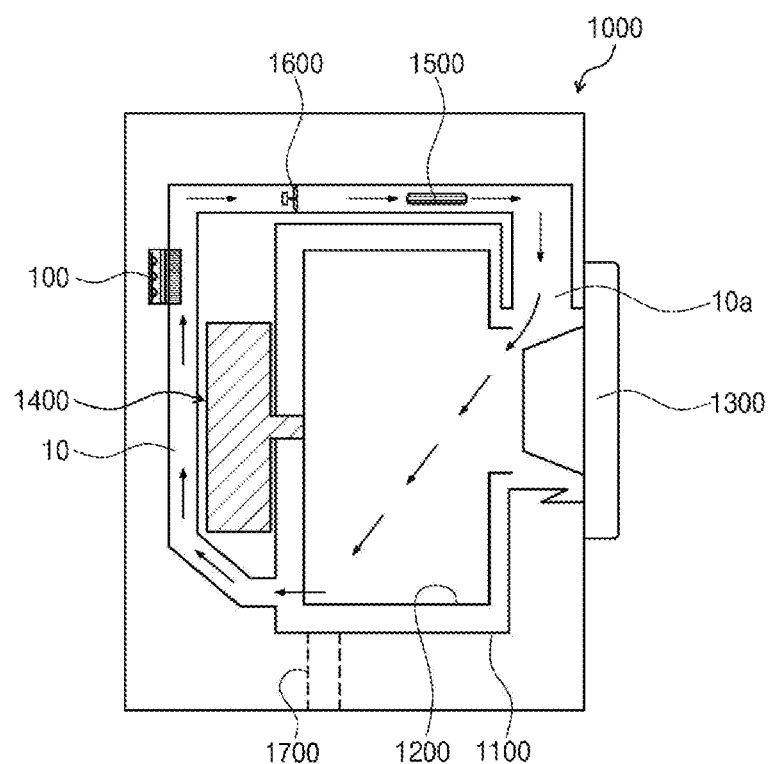
FIG. 17 is a schematic sectional view of one example of the deodorization module according to one embodiment mounted on a washing machine.

FIG. 17 is a schematic sectional view of one example of the deodorization module 100 according to one embodiment mounted on a washing machine 1000.

Referring to FIG. 17, a washing machine 1000 supporting a drying function is provided. As the washing machine 1000, a drum type washing machine will be described for convenience. However, it should be understood that the drum type washing machine is provided by way of example and the deodorization module according to the present disclosure may be applied to a general washing machine, a dryer, and the like.

The washing machine 1000 includes a tub 1100 storing water therein, a drum 1200 rotatably disposed inside the tub 1100 and receiving laundry from the outside, a door 1300 closing or opening the drum 1200, a drive motor 1400 rotating the drum 1200, a drying heater 1500 heating air supplied into the drum 1200, a flow channel 10 along which hot air heated by the drying heater 1500 is supplied to the drum 1200, a blower fan 1600 forcibly blowing the hot air heated by the drying heater 1500 to flow into the drum 1200, and a water discharge unit 1700 discharging the water from the washing machine. A hot air discharge port 10a of the flow channel 10 is placed at a front side of the drum 1200 and a humid air recovery port 10b of the flow channel 10 is placed at a rear side of the drum 1200.

The deodorization module 100 according to the embodiment of the present disclosure is provided to the flow channel 10. In this structure, the deodorization module 100 may be disposed at a higher place than at least the water discharge unit 1700 in order to prevent water from entering the light source unit 140.

As shown in FIG. 17, the deodorization module 100 may be disposed at the rear side of the drying heater 1500, without being limited thereto. Alternatively, the deodorization module 100 may be disposed in front of the drying heater 1500. As such, the deodorization module 100 is disposed inside the flow channel 10 of the washing machine 1000 supporting the drying function, thereby enabling deodorization of dried clothes and washing.

Figure 18:
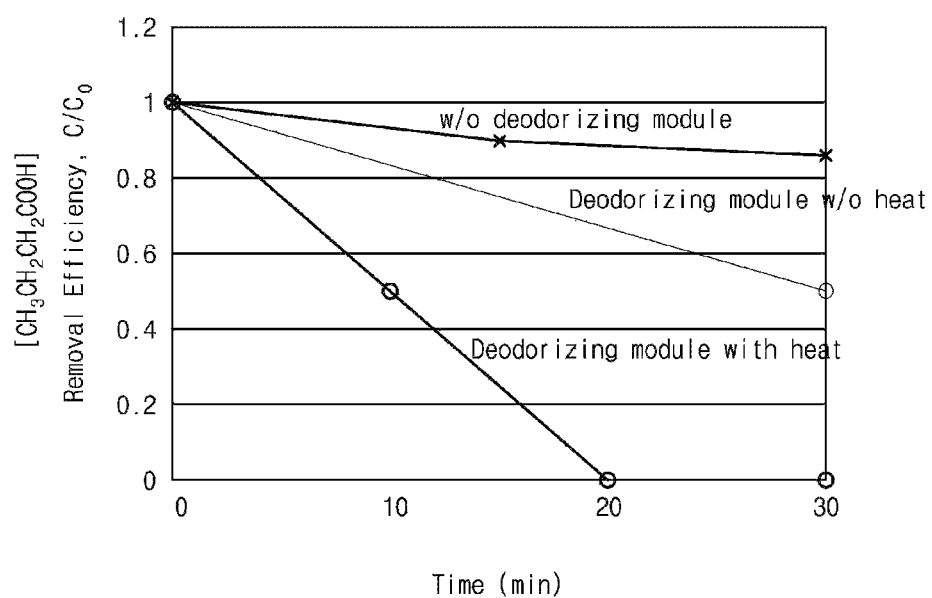
FIG. 18 is a graph depicting effects of the deodorization module according to the present disclosure.

FIG. 18 is a graph depicting effects of the deodorization module 100 according to the embodiment of the present disclosure.

First, in FIG. 18, it can be seen that the deodorization module 100 according to the embodiment of the present disclosure improves a deodorization effect.

In addition, it can be seen that the most efficient deodorization is achieved upon simultaneous operation of the drying heater 1500 and the deodorization module 100. Accordingly, it is desirable that the washing machine 1000 be driven to operate the deodorization module 100 and the drying heater 1500 at the same time.

In this case, however, there is a concern of damage to the light source unit 140 of the deodorization module 100 due to hot air. Accordingly, the washing machine 1000 may be controlled to allow simultaneous operation of the deodorization module 100 and the drying heater 1500 only when the deodorization module 100 includes an additional heat dissipation structure (see FIG. 13A and FIG. 13B). That is, for example, when the deodorization module 100 does not include an additional heat dissipation structure, the washing machine 1000 may be controlled to allow the deodorization module 100 to perform a deodorization operation after completion of a drying operation of the drying heater 1500.

Although some exemplary embodiments have been described herein, it should be understood by those skilled in the art that these embodiments are given by way of example only, and that various modifications, variations, and alterations can be made without departing from the spirit and scope of the present invention. In addition, although advantageous effects provided by a certain configuration are not clearly described in description of the exemplary embodiments, it should be noted that expectable effects of the corresponding configuration should be acknowledged.

What is claimed is:

1. A deodorization module provided to a flow channel, the deodorization module comprising:
   an upper housing open at a top surface and a lower surface thereof;
   a lower housing coupled to the upper housing;
   a photocatalytic filter received in the upper housing through the top surface of the upper housing and disposed inside the flow channel in which air flows in a first direction;
   a light source unit comprising at least one light source adapted to emit ultraviolet light towards the photocatalytic filter and a substrate on which the at least one light source is mounted; and
   a transparent layer disposed between the photocatalytic filter and the light source unit and received in the upper housing through the lower surface of the upper housing, wherein the transparent layer is configured to shield the photocatalytic filter and the light source unit from each other by preventing a fluid communication between the photocatalytic filter and the light source unit;

wherein the photocatalytic filter, the transparent layer, and the light source unit are sequentially disposed along a second direction perpendicular to the first direction, and wherein the deodorization module is arranged in and adjacent to the flow channel such that at least a part of the photocatalytic filter is disposed inside the flow channel and configured to contact and clean air flowing inside the flow channel and that the light source unit is disposed outside the flow channel and is free from contact with the air flowing inside the flow channel.

2. The deodorization module according to claim 1, wherein the lower housing has an open top surface and the light source unit is received in the lower housing through the open top surface of the lower housing.

3. The deodorization module according to claim 1, wherein the upper housing comprises:
a filter securing portion protruding from an upper portion of the upper housing and securing one surface of the photocatalytic filter; and
a filter seating portion protruding along an inner side surface of the upper housing such that another surface of the photocatalytic filter is seated on the filter seating portion.

4. The deodorization module according to claim 3, wherein the upper housing further comprises:
at least one opening formed at a lower end of the filter seating portion to expose an interior of the upper housing; and
at least one rib formed in the at least one opening.

5. The deodorization module according to claim 4, wherein the upper housing further comprises:
a spacer protruding from a lower end of the at least one opening and contacting one surface of the transparent layer.

6. The deodorization module according to claim 5, wherein the lower housing comprises:
a spacer protruding from an upper end of the lower housing and contacting another surface of the transparent layer.

7. The deodorization module according to claim 6, wherein the lower housing further comprises:
at least one securing protrusion protruding from a lower surface of the lower housing and securing the light source unit.

8. The deodorization module according to claim 7, wherein the lower housing further comprises:
a heat dissipation hole formed on the lower surface of the lower housing and corresponding to a shape of the light source unit; and
a withdrawal hole through which an electric wire connected to the light source unit is withdrawn outside.

9. The deodorization module according to claim 4, wherein the one surface of the photocatalytic filter is exposed in the flow channel through the top surface of the upper housing and another surface of the photocatalytic filter is accessible to the air inside the flow channel through the at least one opening.

10. The deodorization module according to claim 1, further comprising:
a heat dissipation member contacting the light source unit and discharging heat from the light source unit.

11. The deodorization module according to claim 1, wherein the substrate is a heat dissipation substrate.

12. The deodorization module according to claim 1, further comprising:
a reflective plate disposed inside the flow channel and reflecting light emitted from the light source unit.

13. The deodorization module according to claim 12, wherein the reflective plate is slanted at a predetermined angle with respect to the photocatalytic filter.

14. The deodorization module according to claim 1, further comprising:
a flow channel guide disposed inside the flow channel to be slanted at a predetermined angle with respect to the photocatalytic filter and having at least one surface coated with a reflective material.

15. The deodorization module according to claim 1, wherein the photocatalytic filter is disposed to extend in a direction perpendicular to an air flowing direction.

16. The deodorization module according to claim 1, wherein the photocatalytic filter is slanted at a predetermined angle with respect to an air flowing direction.

17. The deodorization module according to claim 16, wherein the light source unit is disposed parallel to the photocatalytic filter slanted at the predetermined angle with respect to the air flowing direction.

18. A drying apparatus comprising:
a drum into which laundry is input;
a drying heater configured to heat air to provide heated air to be supplied into the drum;
a flow channel along which the heated air is supplied into the drum;
a blower fan blowing the heated air to flow into the drum; and
a deodorization module provided to the flow channel and deodorizing the heated air, the deodorization module comprising:
an upper housing open at a top surface and a lower surface thereof;
a lower housing coupled to the upper housing;
a photocatalytic filter received in the upper housing through the top surface of the upper housing and disposed inside the flow channel in which air flows in a first direction;
a light source unit comprising at least one light source adapted to emit ultraviolet light towards the photocatalytic filter and a substrate on which the at least one light source is mounted; and
a transparent layer disposed between the photocatalytic filter and the light source unit and received in the upper housing through the lower surface of the upper housing, wherein the transparent layer is configured to shield the photocatalytic filter and the light source unit from each other by preventing a fluid communication between the photocatalytic filter and the light source unit;

wherein the photocatalytic filter, the transparent layer, and the light source unit are sequentially disposed along a second direction perpendicular to the first direction, and wherein the deodorization module is arranged in and adjacent to the flow channel such that at least a part of the photocatalytic filter is disposed inside the flow channel and configured to contact and clean air flowing inside the flow channel and that the light source unit is disposed outside the flow channel and is free from contact with the air flowing inside the flow channel.

19. The drying apparatus according to claim 18, wherein the drying heater and the deodorization module are substantially simultaneously in operation.

20. The drying apparatus according to claim 18, wherein the deodorization module is in operation subsequent to completion of a drying operation.

\* \* \* \* \*